Figure 2:
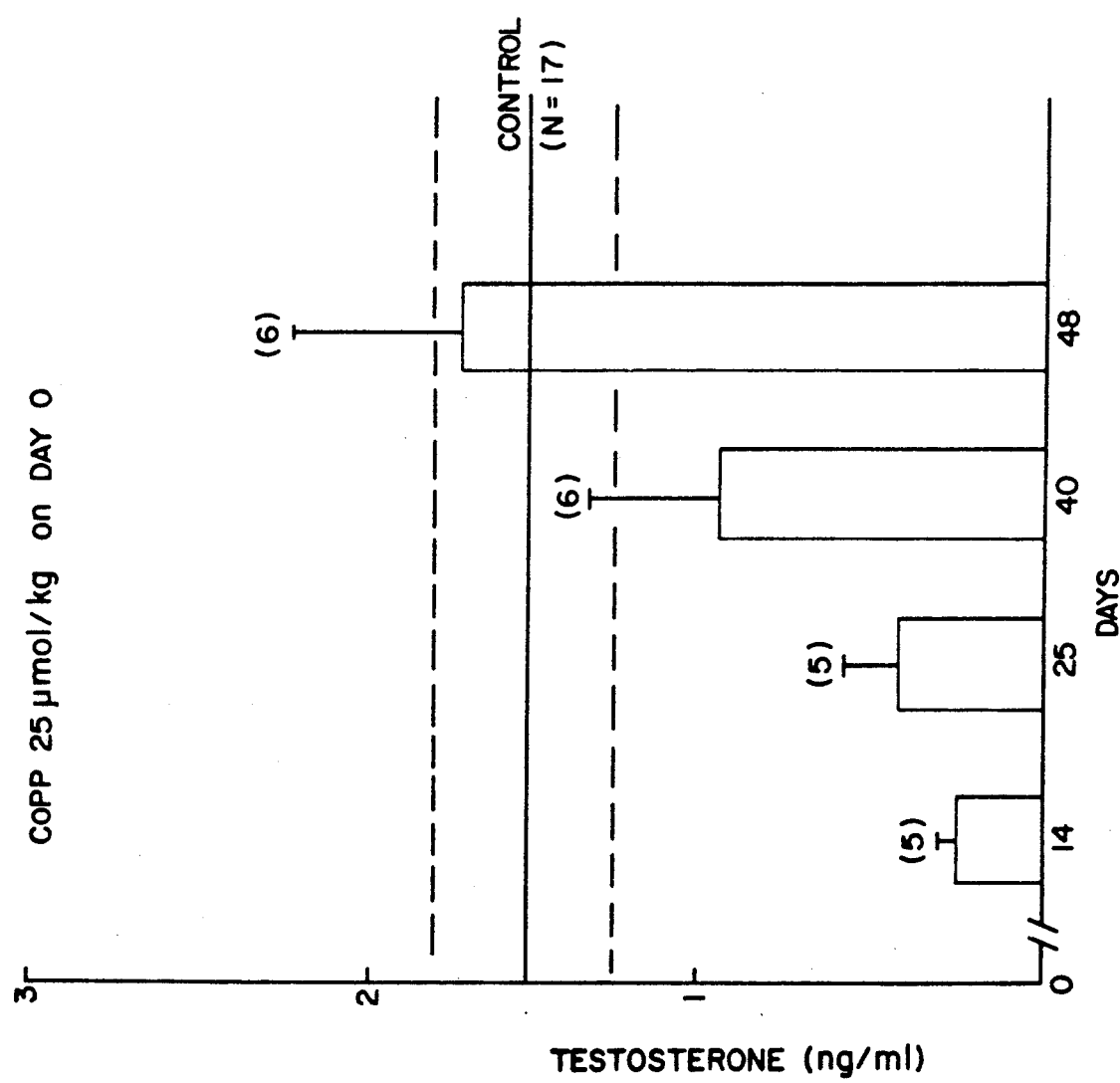

United States Patent [19]

Kappas et al.

[11] Patent Number: 5,066,650
[45] Date of Patent: Nov. 19, 1991

[54] METHOD FOR SUPPRESSING THE ENDOCRINE SYSTEM

[75] Inventors: Attallah Kappas; George S. Drummond, both of New York, N.Y.

[73] Assignee: The Rockefeller University, N.Y.

[21] Appl. No.: 638,623

[22] Filed: Jan. 8, 1991

Related U.S. Application Data

[60] Division of Ser. No. 498,289, Mar. 23, 1990, which is a continuation-in-part of Ser. No. 105,591, Nov. 13, 1987, abandoned, which is a continuation-in-part of Ser. No. 927,830, Nov. 6, 1986, abandoned, which is a continuation-in-part of Ser. No. 832,512, Feb. 21, 1986, abandoned, and a continuation of Ser. No. 708,228, Mar. 5, 1985, abandoned, which is a continuation-in-part of Ser. No. 363,588, Mar. 30, 1982, abandoned.

[51] Int. Cl.$^5$ .............................. A61K 31/555
[52] U.S. Cl. ...................... 514/185; 514/410
[58] Field of Search .................. 514/185, 410

[56] References Cited

U.S. PATENT DOCUMENTS 4,393,071  7/1983  Fujii et al. ...................... 514/410
4,948,792  8/1990  Kappas et al. ...................... 514/185

OTHER PUBLICATIONS

Davis et al., J. Lab. Clin. Med. 95(3) 1980, pp. 714–724.
Smith et al., Proc. Natl. Acad. Sci. 79, 7537–7541, 1982.
Hadley et al., Endocrinology [1984, Prentice Hall, Englewood, N.J.] pp. 429 to 433.
Smith et al., Pharmacology 34, 9–16 (1986).
Gilbraith et al., Pharmacology 34 241–249, 1987.
Gilbraith et al., Neuroendocrinology 1989; 49:641–648
Belovetskaya, Chemical Abstracts, vol. 100, 1983, Abstract 45779k.
Kitchin K. T.; J. Biochem. 12(4), 479–485, 1981.
Feuer et al., Xenobiotica 1985, 15(5) 407–412

Primary Examiner—Mukund J. Shah
Assistant Examiner—E. C. Ward
Attorney, Agent, or Firm—Wyatt, Gerber, Burke and Badie

[57] ABSTRACT

Method for limiting the production of estrogenic steroids by parenteral administration of selected amounts of cobalt protoporphyrin or cobalt mesoporphyrin.

5 Claims, 5 Drawing Sheets

FIG. IA
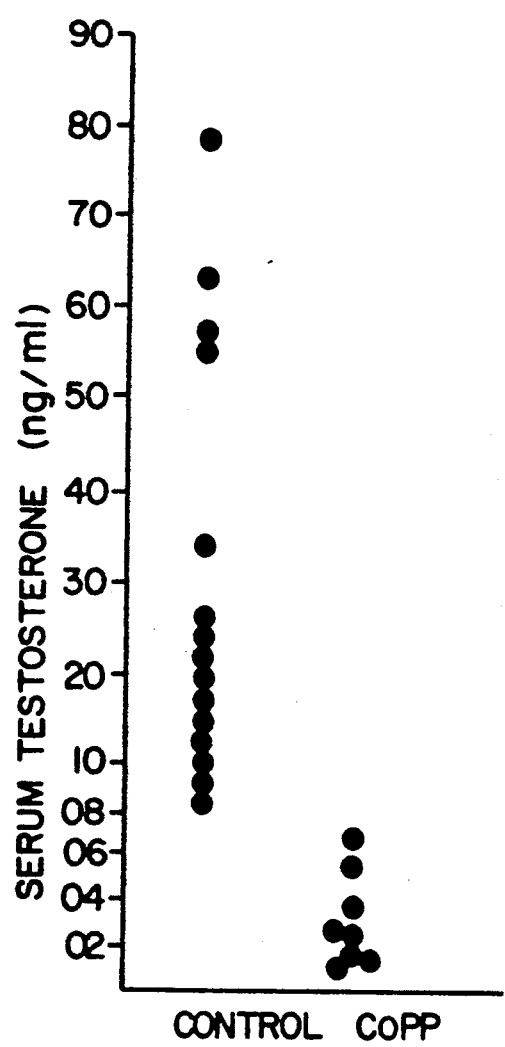
FIG. IB
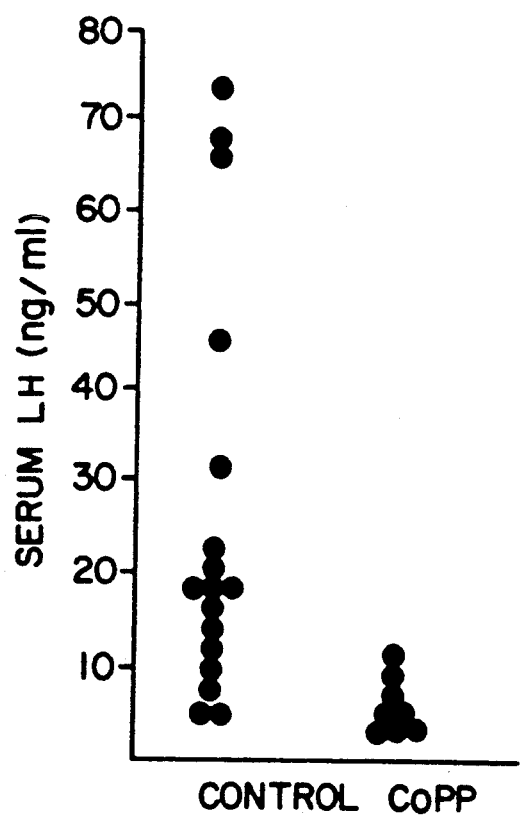

METHOD FOR SUPPRESSING THE ENDOCRINE SYSTEM

RELATED APPLICATIONS

This application is a division of application Ser. No. 07/498,289 filed Nov. 23, 1990, which is a continuation in part of copending patent application Ser. No. 105,591, filed Nov. 13, 1987 now abandoned, which is a continuation in part of patent application Ser. No. 927,830, filed Nov. 6, 1986 now abandoned which is, in turn, a continuation in part of patent application Ser. No. 832,512 filed Feb. 21, 1986, now abandoned. The latter application is a continuation of patent application Ser. No. 708,228 filed Mar. 5, 1985 and now abandoned, which is, in turn a continuation in part of patent application Ser. No. 363,588 filed Mar. 30, 1982, now abandoned.

This invention is concerned with methods of suppressing the endocrine system of animals. More particularly, it is concerned with methods for limiting the activity of the glands of the endocrine system to achieve desirable physiological results such as suppression of hormone production of animals, i.e., living beings including mammals such as man; bovines, particularly beef cattle; sheep; goats; poultry, especially chickens, ducks and turkeys; as well as fish, particularly those raised in fish farms such as salmon and trout; and, in general, all animals of economic importance in addition to pets by treatment with cobalt protoporphyrin (CoPP) or cobalt mesoporphyrin (CoMP). It is concerned also with therapeutically useful isotonic compositions containing CoPP and/or CoMP. Both of these compounds are known.

The endocrine system is responsible for the production and distribution in animals of hormones which influence such factors as phenotype, homeostasis, size and behavior of the individual as well as weight and weight factors such as protein to fat ration (P/F). The principal organs of the endocrine system are the hypothalamus, pituitary (anterior and posterior), parathyroid, thyroid, thymus adrenal, pancreas and gonads (testes in male and ovaries in females). The organs of the system secrete one or more hormones which aid in the proper metabolic function of a target organ. For example, ADH, an antidiuretic hormone, sometimes called vasopressin secretes from the posterior pituitary gland to promote the reabsorption of water by the kidney. This is thought to be regulated by the hypothalamus.

The hypothalamus is believed to regulate the secretion of the antidiuretic hormone ADH. When specialized cells of the hypothalamus sense that the blood lacks sufficient water, ADH is released by the hypothalamus nerve fibers for secretion by the posterior pituitary. ADH travels in the bloodstream to its target organ, the kidney. There it promotes the reabsorption of water so that the blood becomes more dilute. As the blood becomes more dilute because of the reabsorbed water, this fact is sensed in the hypothalamus, and production of the ADH ceases.

In some instances, the target organ of one endocrine gland is a second gland in the same system. For example, the trophic hormones of the anterior pituitary, e.g., luteinizing hormone (LH), stimulate the gonads to produce androgens, such as testosterone, estrogen and progesterone.

Growth hormone (GH) produced in the anterior pituitary dramatically affects the phenotype of mammals since it determines the size of the individual. It causes protein accumulation in almost all of the cells of the body. In response to GH, all tissues of the body including bones grown. The bones continue to grow during childhood as long as a small area of cartilage remains at both ends. Growth ceases when this area of cartilage is replaced by bone. The long bones have completed their growth at the onset of adulthood.

The amount of GH produced during the early prepubertal years determines the size of the individual. If the production is too low, or completely absent, the person will become a midget. If too much GH is produced the person will become a giant.

If the production of GH increases in the adult only the bones of the jaw, eyebrows, nose, fingers and toes can respond. When these begin to grow, the person takes on an unusual appearance characterized by very large fingers and toes. This condition is one result of hyperpituitarism. It is specifically identified as acromegaly. It is believed that the biblical figure Goliath had acromegaly. Other such conditions are known and recognized.

In instances where there is an overproduction of hormones which may be manifested by undesirable weight gain or increase in growth rate, or where there is an undesirable response to normal production of hormones, it would be useful to suppress the production of the offending hormone or hormones. Such a method has now been discovered.

It has been found that it is possible to suppress the endocrine system of mammal by treatment with a selected metalloporphyrin thereby making it possible to treat various human afflictions associated with over activity of one or more of the glands of the endocrine system. More specifically, it has been observed that the administration to animals of CoPP strongly stimulates heme oxygenase activity while at the same time suppressing ALA synthetase activity and markedly suppressing the endocrine system.

A particularly valuable aspect of this invention is the ability of CoPP and CoMP to limit the production of the gonadal androgenic and esterogenic hormones such as testosterone and estrogen, and to limit the production of the thyroid hormones.

The gonadal hormones have anabolic activity. They are their synthetic analogs are employed to promote growth. Overproduction of the anabolic hormones leads to an increased growth rate associated with increased food intake. It has been discovered that one of the immediate effects of the administration of CoPP or CoMP to animals is a prompt decrease in appetite and subsequent growth rate. This continues during the period when the concentration of gonadal hormones is below that of untreated mammals. Surprisingly, the decreased growth rate continues long after the gonadal level has returned to normal. In rats, as will be explained below, the low testosterone level continues for at about 48 days, but the decreased growth rate continues for at least 90 to 100 days. In other respects the animal appears to be normal except that the P/F ratio is increased. The period of the decreased testosterone level may be controlled for selected periods of time by selection of the amount of CoPP or CoMP administered.

The decreased growth rate observed in animals can be maintained beyond the 90 days or other originally selected period by further administration of CoPP or CoMP, typically at a lower dosage level. Thus CoPP or CoMP can be used in animals to attain and maintain decreased growth rates, thereby assisting in weight control. As will be explained more fully hereinafter, the P/F ratio in the body of an animal treated with either of these metallic salts is appreciably increased.

As shown below, CoPP administered to rats results in a very marked depletion of the thyroid hormones, $T_3$ and $T_4$ as well as lower than expected levels of the pituitary derived trophic hormone, TSH in animal plasma. Additionally, in such treated animals there is a loss of gonadal hormones such as testosterone and estrogen from plasma and a concurrently lower than normal level of the pituitary derived trophic hormone, LH. It has also been observed on the hypothalamus — pituitary — adrenal axis that there is a suppression of cortisol in plasma.

These finding indicate that the peripheral endocrine system as represented by the thyroid, gonads and adrenals is suppressed and that the result is related to suppression of the synthesis or release or pituitary hormones. Microscopic examination of the pituitary indicate that the thyroid releasing cells (TSH) are markedly smaller in the CoPP treated animals than in normal control animals.

The figures show the results of studies conducted with rats, and clearly illustrate the activity of CoPP to suppress the activity of the endocrine system. Similar results are obtained with CoMP.

FIG. 1, panels A and B, depicts graphically the results of experiments showing the CoPP suppresses the endocrine system in rats. Specifically, in this example, it si shown that the aspect of the endocrine system involving the pituitary-testicular axis is suppressed. Panel A of FIG. 1 shows serum testosterone levels in rats which received 2 does, each does being 50 um/kg body weight of CoPP with hormone determinations being made 7 days after the initial injection. As can be seen in the control column on the left, serum testosterone levels before treatment with CoPP were within the range expected in this animal species. In the group of data shown in the right column of this panel (marked CoPP), the levels of serum testosterone after CoPP administration are all below 0.8 ng/ml which is an extraordinary drop in the serum level of this male sex hormone. In panel B on the right, data shown serum LH levels, which controls the synthesis and release of testosterone from the gonads and which itself is produced and released by the pituitary under hypothalamic stimulation, are shown. The control group shows the range of normal levels of serum LH which are characteristic of this animal species. The data for CoPP shown at the right of this panel indicate that there was no compensatory increase in serum LH release from the pituitary as would normally be expected despite the profound decline in serum testosterone levels shown in the left panel of this figure.

In these studies, the dosage level of CoPP was 50 umol/kg of body weight. The number of animals is indicated by the number of dots.

There is known to be a feed-back regulatory endocrine mechanism in which the peripheral and central endocrine glands, i.e., pituitary — gonadal axis in this case, act in concert to keep hormone levels at an appropriate constant level of equilibrium. Thus, if serum testosterone levels markedly decline, there should be a striking increase in serum LH levels to restore serum testosterone levels to normal. In contrast to that expected increase, the CoPP treated animals showed no such compensatory increase whatsoever, as can be clearly seen from FIG. 1 B. This indicates that the compensatory mechanism for stimulating an enhanced output of serum testosterone had been impaired by the CoPP and that for reasons which are not clear, the pituitary was unable to release LH which would be required to compensate the disequilibrium in testosterone production produced by CoPP. Thus the decrease in serum testosterone levels in these animals was not compensated by a rebound increase in serum LH which would have brought the serum sex hormone levels back to normal. This indicates a profound decline in endocrine function at both the central and peripheral levels. It strongly suggests that the synthetic metalloporphyrin operates at a level even higher than the pituitary gland and specifically at some point in the axis between the pituitary-hypothalmalus from which releasing hormones (i.e., LH-releasing hormone etc.) are transmitted to the pituitary where they then stimulate the release of such trophic hormones as, in this case, LH.

The results with CoMP are similar.

FIG. 2 shows the duration of the suppression of serum testosterone levels that can be elicited by a single does of 25 umol/kg body eight of CoPP. As indicated, the bars show the level of serum testosterone which on days 14-40 are markedly below normal levels as in consistent with the data in FIG. 1. Hormone levels gradually revert towards normal levels — but do not enter the normal range, until day 48. Thus a single dose of CoPP is capable of profoundly suppressing the synthesis and the release of the gonadal sex and growth hormone testosterone and the synthesis or release of the trophic hormone for gonadal hormone production (LH). This effect can last for 40-48 days after a single injection of either of the metalloporphyrins of this invention. This ability transiently to suppress such an important endocrine complex as the hypothalamus-pituitary-gonadal axis is a novel biological action effected by administration of the herein disclosed metalloporphyrins and clearly shows the utility of these products for treatment of disorders that are provoked by excessive levels of the gonadal hormones. In other studies the suppression depicted here over a term of 48 days, has been extended for as long as 9 months by repeated administration of CoPP at periodic intervals. This clearly indicates that periodic administration of this synthetic metalloporphyrin will provide a useful means for suppressing endocrine function for as long as the compound is administered.

In FIG. 2 the number above each bar is the number of animals tested. The dotted, horizontal lines represent the range observed for levels of testosterone in the control animals.

The suppression of the endocrine system resulting in markedly reduced production of gonadal and thyroid hormones by CoPP and CoMP is reversible. Once the administration of the selected compound ceases, there is a gradual and complete return to normal of the endocrine system. This characteristic of the compounds is of great value in clinical situations in which the degree to which a disorder is responsive to excessive levels of a particular endocrine secretion in now known. It can be determined by judicious use — to suppress endocrine function — of an appropriate dose of CoPP or CoMP, permitting recovery to normal when the effect of the compound has receded. However, although he endocrine system by standard measures returns to normal, the growth rate remains at a reduced level for many more weeks.

Figure 3C:
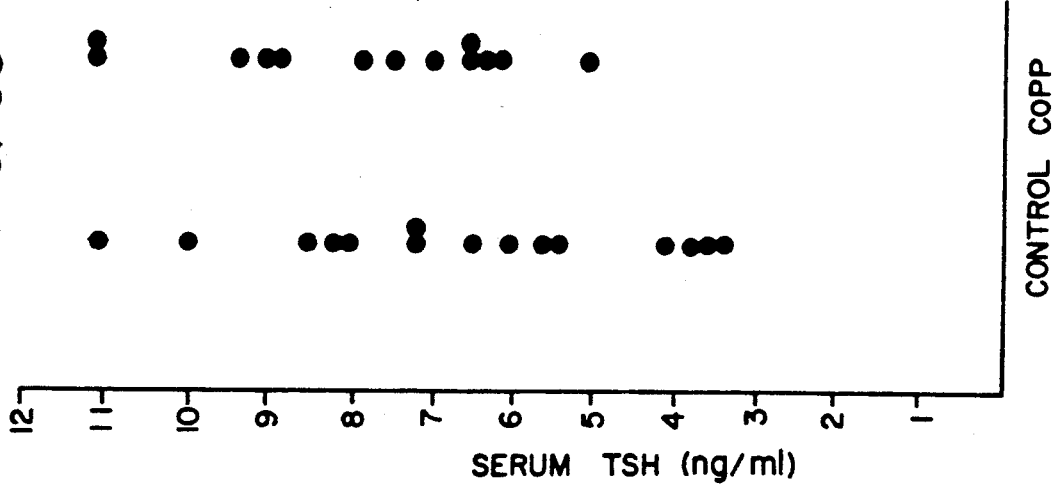
Figure 3B:
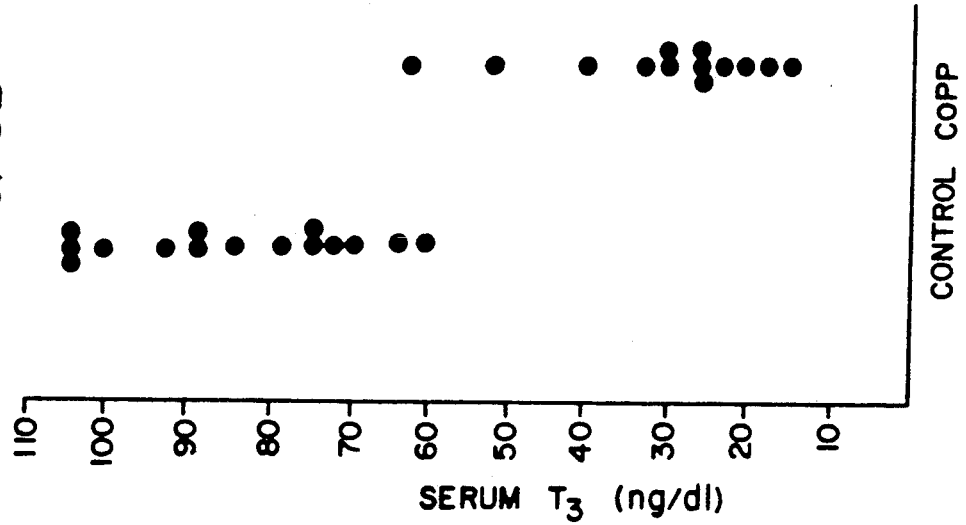
Figure 3A:
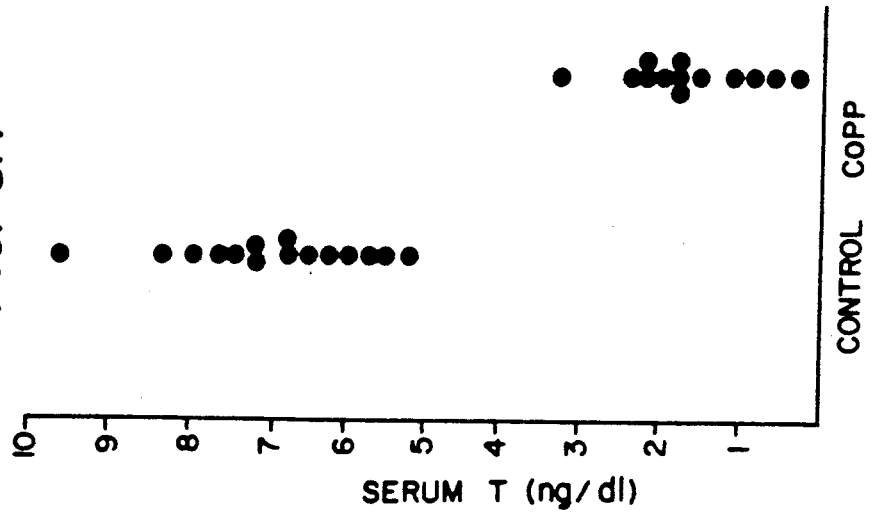

FIG. 3 shows comparable data for the pituitary-thyroid axis. Panel A of the figure shows serum $T_4$ (thyroxin levels in animals and the range over which they fall normally. The column marked CoPP in this panel shows the markedly diminished levels of serum $T_4$ which are produced by treatment of the animals with CoPP (2 times 50 umol/kg b.w.) in the same manner and with the same dosages indicated for the previous studies with the sex hormone, testosterone. Panel B shows a similar decrease in levels of the second major thyroid hormone, $T_3$, its levels in plasma in control animals, and the comparable depleting effect on the plasma levels of this hormone produced by CoPP. Finally, Panel C shows the serum levels of the trophic hormone for the thyroid gland, i.e., thyroid stimulating hormone (TSH), in both control and CoPP-treated animals. In animals including man, when thyroid levels are markedly depleted, as shown in the first two panels of this figure, serum TSH levels will rebound to levels far greater than are seen in control circumstances. However, as panel C indicates, there was of such rebound in these animals was incapable of responding normally to the decreased plasma levels of thyroid hormones ($T_4$ and $T_3$) that was produced by CoPP.

Similar results are observed with CoMP.

These findings together with those in FIGS. 1 and 2 dealing with the pituitary-gonadal axis clearly indicate a hypothalmic effect of the synthetic metalloporphyrins of this invention. This effect could be mediated through an action of the compound on the releasing hormones for the trophic hormones (LH or TSH) which control the peripheral synthesis and secretion of thyroid and gonadal hormones, or by some other mechanism as yet undefined. Thus, in these two major endocrine aces, the synthetic metalloporphyrins CoPP and CoMP exert a profound suppressive effect following administration in relatively small amounts of the selected compound.

It is clear from the results of these studied involving the pituitary-thyroid axis that administration of CoPP is useful to treat mammalian afflictions associated with hyperthyroidism.

Figure 4:
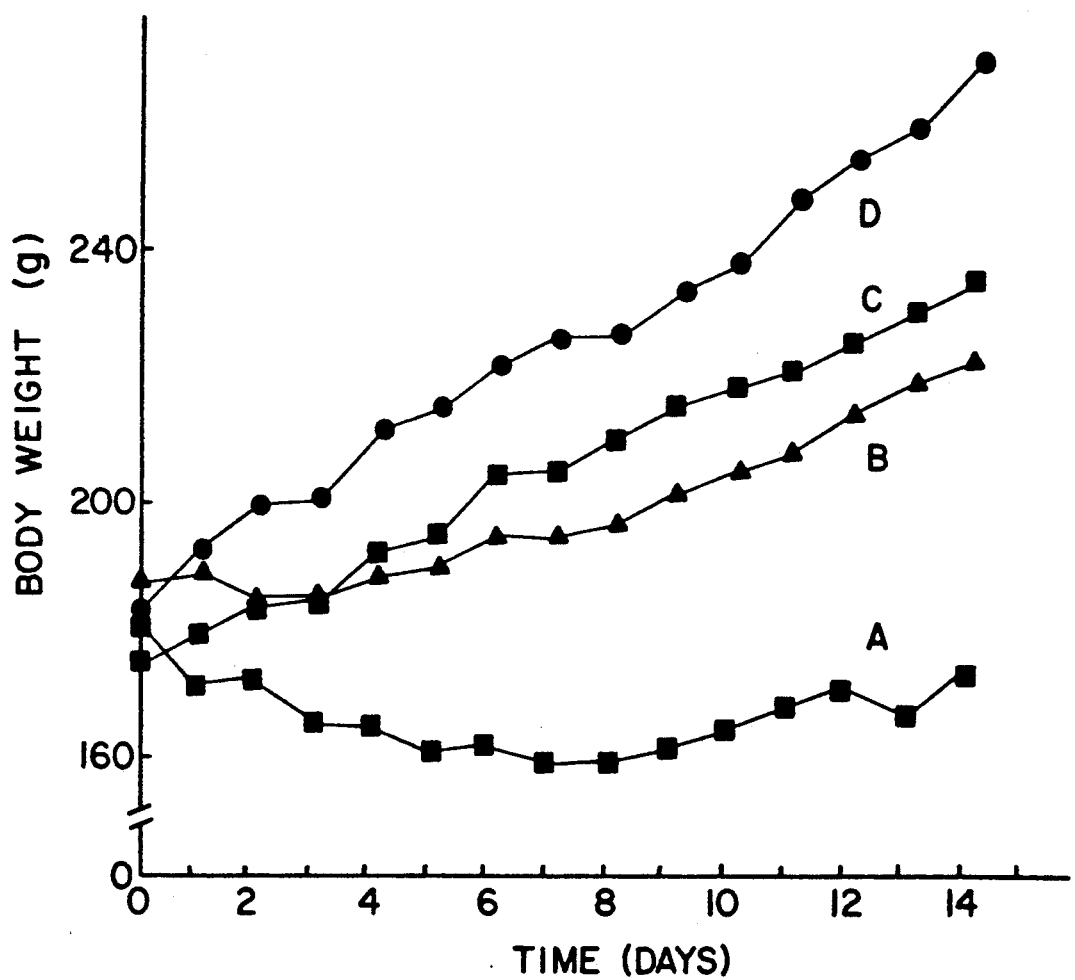

FIG. 4 shows the observed weight loss after a single dose of CoPP treatment of male Sprague-Dawley rats (140-160 g).

The parenteral solutions used in this study and other studies reported herein can be prepared by dissolving CoPP or CoMP in a small volume of 0.1 M NaOH (0.1 ml/ml of the metalloporphyrin solution). The CoPP and CoMP were purchased from Porphyrin Products (Logan, Utah). The pH of the solution was adjusted to 7.4 with 1M HCl, and the final volume was adjusted by the addition of 0.9% NaCl solution. Treatment was by subcutaneous injection.

In the study, the rats were treated on day zero with the following solutions:
50 umol/kg bw A
25 umol/kg bw B
5 umol/kg bw C
saline D Each point in the figure represents the mean body weight of 6 animals.

It will be seen that after an initial cessation of, or decline in, rate of growth, rats treated with 5-25 umol/kg b.w. gained at a rate parallel to, but below that of saline treated controls. Rats treated with 50 umol/kg b.w. lost weight immediately and had not returned to their starting weight even after 14 days. However by day 14 they had started to gain weight at a rate parallel to the controls.

Figure 5:
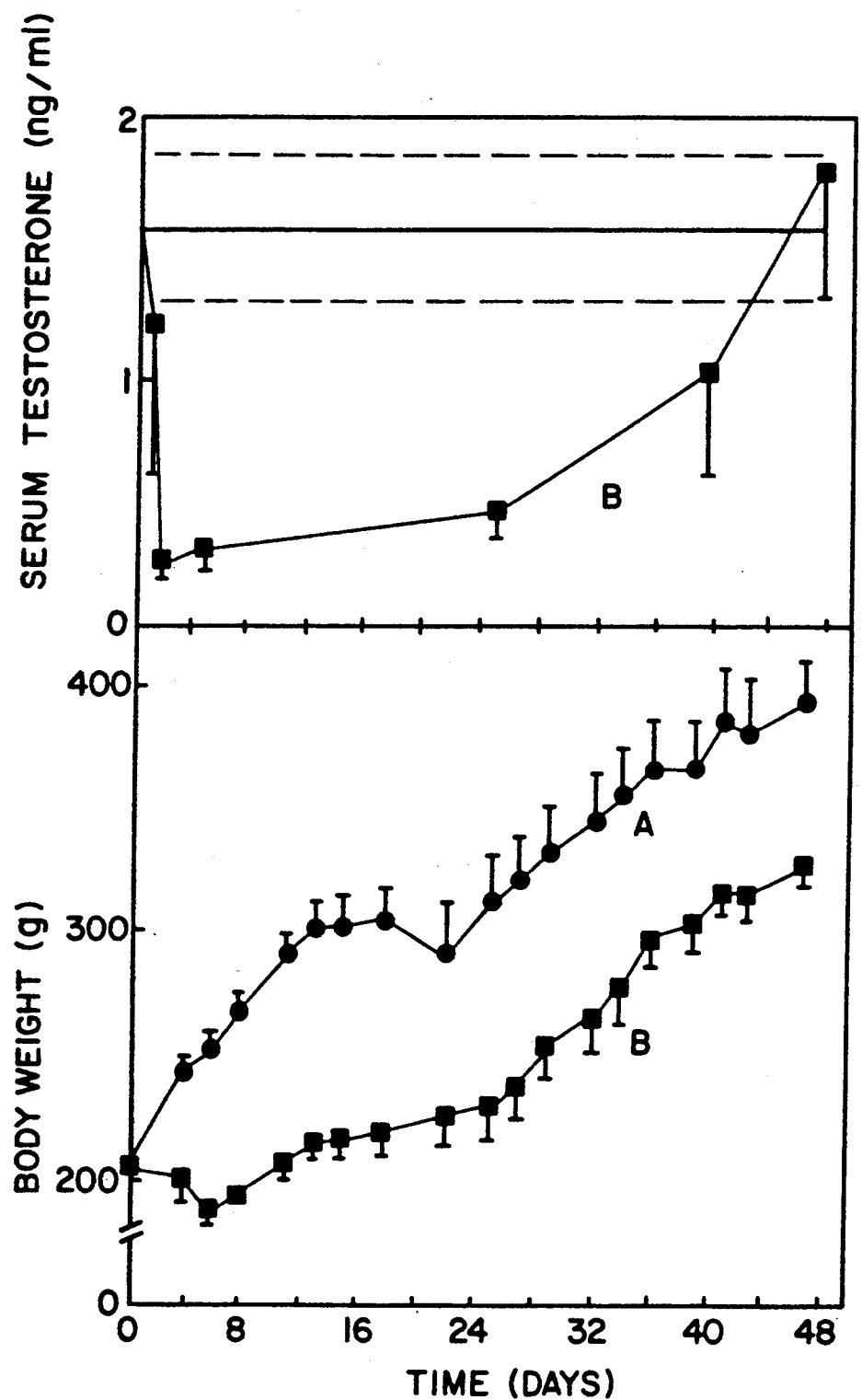

FIG. 5 shows a relationship between testosterone concentration and weight loss. The lower panel, shows the daily weight $\pm$SEM of 6 rats treated with saline, a, or CoPP at 25 umol/kg b.w. At the times indicated tail blood was collected and serum testosterone concentration measured (upper panel). The value $\pm$SEM of 6 treated rats B are shown in the upper panel.

In this study serum testosterone levels declined by about 90% within 4 days. Weight gain remained constant during this 4 day period, dropped slightly in the ensuing week, and resumed in succeeding weeks, paralleling controls from about day 20 to day 48. Untreated animals gained weight steadily throughout the study period. Within the time period from 4 to 25 days, serum testosterone levels remained at markedly low levels and thereafter returned toward normal which they reached after about 40 to 48 days.

Despite the fact that treated animals reverted to a rate of weight gain paralleling that of the controls, even when their serum testosterone levels had normalized, their total body weights remained consistently about 25% lower than those of untreated animals. It was noted that this disparity continued for as long as 90 to 100 days. Similar results are observed in female rats by studying the relationship between estrogen levels and weight gain.

Another very significant effect of the administration of CoPP or CoMP is the marked increase in the P/F ratio in the treated animal.

In one experiment illustrating this unusual and valuable result, 40 young Sprague-Dawley rats (160-200 g) were divided into 5 equal groups of animals. One group was administered saline and served as control group. The remaining 32 animals were treated parenterally with 1 umol/kg body weight of CoPP and observed during a 180 day period. Eight of these animals received no further treatment. At the end of two weeks the remaining 24 animals received a second identical dose of CoPP. The sequence was repeated at two week intervals utilizing successively 16 and 8 animals from the original group. Thus, in addition to the control group, there were four groups of animals who received a total of 10, 20 30 and 40 umol/kg body weight of CoPP respectively. At the end of 180 days all animals were sacrificed and the total fat and protein in their bodies determined. The results are shown in the following table.

TABLE 1

| GROUP | | % FAT | % PROTEIN | P/F RATIO |
|---|---|---|---|---|
| Control | Saline | 19.6 | 19.6 | 1.00/1.0 |
| 1 | (CoPP 1 × 10 umol/kg bw) | 16.6 | 20.7 | 1.25/1.0 |
| 2 | (CoPP 2 × 10 umol/kg bw) | 14.5 | 20.4 | 1.41/1.0 |
| 3 | (CoPP 3 × 10 umol/kg bw) | 13.3 | 21.6 | 1.62/1.0 |
| 4 | (CoPP 4 × 10 umol/kg bw) | 12.4 | 21.4 | 1.73/1.0 |

It will be observed that there has been a constant decrease in the percent of body fat with increasing doses of CoPP. The ultimate decrease in body weight at the highest dose of CoPP is 41%. This decrease in fat content occurs without a statistical increase in the percent protein resulting in a consequent major increase in the P/F ratio from 1.0/1.0 to 1.73/1.0. The same effect can be achieved by one dose of the selected metalloporphyrin as with a series of treatments.

Those skilled in the art of animal husbandry will recognize the economic significance of this aspect of the invention. It is now possible to produce economically important animals such as beef cattle and poultry with edible tissues of less fat content and proportionately increased protein content. This is enormous importance in animal husbandry for a number of reasons. The first of these is that the animals utilize their feed more efficiently. Normally it requires more food, and therefore more expense, to produce a pound of fat than to produce a pound of protein. The body of an animal treated in accordance with this invention will have less fat and therefore a higher protein to weight ratio than an untreated animal. The edible tissues of the treated animal will have more nutritional value than the tissues of untreated animals.

A second important consequence is that the edible meat produced by the treated animal will have decreased fat content compared to untreated animals. Recent studies make it more and more evident that high protein, i.e., lean meat is more healthy for human consumption than meat with a high fat content.

It has long been recognized that fish caught in fresh rivers, and lakes or in salt water are more flavorful that the same species raised in fish forms. This is because the tissues of the latter fish have a higher fat content. Application of this invention will, therefore, have a profound impact on this industry.

Duck meat is not as poplar as chicken or turkey meat. This fact is usually attributed to the high fat content of duck tissue. The use of CoPP or CoMP should increase the popularity of duck as a comestible.

It appears that the administration of CoPP or CoMP to animals has at least three effects. These are:
1. A transient decrease in gonadal hormone production with a concommitant decrease in anabolic growth promoting activity.
2. A long term appetite suppressing effect possibly by action of the compounds on some appetite regulatory site in the hypothalmus.
3. An increase in the P/F ration.

It should be noted that endocrine studies in animals have served as valid and art recognized models of the regulatory mechanisms by which the endocrine control systems in humans operate. Thus, for example, the seminal work by Huggins on the role of male sex hormone in the pathogenesis of prostatic hypertrophy and the effects thereon of castration (removal of the male sex hormone, testosterone, by removing the testes) with resulting remission of the hypertrophic prostate condition was done in dogs. Similarly, the elucidation of the principal regulatory mechanisms for thyroid hormone have been carried out in rats and other animals, and the results observed have proved to be reliable indicators of analogous results in humans thus permitting accurate predictions of therapeutic results to be achieved by administration to humans of agents tested in animals. Thus, these animal models of endocrine suppression by the CoPP have full relevance to the circumstances existing in humans and clearly indicate that in selected doses the synthetic metalloporphyrins CoPP or CoMP will suppress the endocrine system in humans and other mammals.

The newly discovered ability markedly but transiently to suppress the endocrine system of mammals as described and illustrated herein has very important clinical consequences because there are circumstances in which the extend to which a certain condition, for example a hypertrophic growth condition in the prostrate or thyroid is hormone-sensitive is now known. In the past, this problem has often forced the physician to extirpative surgery (castration, thyroidectomy, hypophysectomy, etc.). As a result of this discovery, it is now very simple to administer small doses of CoPP or CoMP to suppress the endocrine system (with selective replacement of hormones not suspected of being provocative agents) and determine the effect of the suppression on the course of the condition in question. Following the obtaining of such information, therapy is then continued with the selected metalloporphyrin to maintain suppression of the endocrine system or selective surgical alteration of the appropriate endocrine gland could be carried out if warranted.

The selected compounds of the invention will normally be administered parenterally, i.e., intraveneously, subcutaneously or intramuscularly in sterile, parenteral, isotonic solutions. For such solutions any of a wide variety of pharmaceutically acceptable carriers currently in sue for the preparation of parenteral compositions may be employed. The solutions may be buffered for example with a phosphate buffer to a pH of about 7 to 8, preferably 7.4 to 7.5, and contain solutes such as saline or glucose. The solutions may also contain a polyhydoxy alcohol such as ethylene or propylene glycol. The active compounds may also be administered in solution or suspension in a sterile, inert oil such as sesame or safflower oil. A typical dosage regimen will be two separate administrations per week at a dosage rate of 5 to 50 umol/kg of body weight. The physician or veterinarian will determined the specific dosage, and it will depend upon such well understood factors as the condition under treatment, age, weight and general health of the patient.

At the levels of administration disclosed and claimed herein all of the disclosed effects will proceed simultaneously. There will be suppression of the endocrine system, weight loss and improved P/F ratio. If for any reason the suppression is not acceptable the necessary counteracting hormones can be separately administered. Alternatively the CoPP or CoMP can be administered at a lower dosage where endocrine suppression is no longer a factor as disclosed in copending and commonly owned patent application (Docket 18112).

Typically, an isotonic solution can be prepared by dissolving the selected amount of CoPP or CoMP in 0.1 M aqueous sodium hydroxide solution, adjusting to the selected pH with 1 M hydrochloric acid, and making up to volume with 0.9 aqueous sodium chloride solution. The concentration of active agent in the parenteral composition may be from about 1 to 25 mg/ml.

The administration of the active agent appears to suppress the complete endocrine system but is particularly valuable for limiting the production of gonadal and thyroid hormones, for controlling weight, and for increasing the P/F ratio in animals. Therefore, as suggested above, if the active agent is administered therapeutically to control one endocrine function, e.g., secretion of thyroid hormone, there will be a concurrent treatment with other supplement hormones, all of which are available commercially, to compensate for the suppression of other endocrine functions.

The suppressive effect of CoPP and CoMP recedes with time and the subjects revert to their normal state except as to growth rate, ultimate body weight, and P/F ratio. This occurs during variable periods of time depending on the dosage of the metalloporphyrin. Thus therapeutic treatment can be continued for selected periods to correct or alleviate a specific condition. It may be interrupted after a first course of treatment, or it may be continued for differing period of times at different levels.

Inorganic cobalt, iron protoporphyrin (heme), tin protoporphyrin and other metalloporphyrins studied do not have the effect of CoPP an CoMP. It presently appears that the requirements for endocrine system suppression are that the metalloporphyrin be capable of stimulating for extended periods of time the catalytic activity of heme oxygenase 5 to 15 fold in the liver and perhaps pituitary glands and hypothalmus while simultaneously suppressing ALA-synthetase and cytochrome P-450 activity in these organs. These enzymes are the rate limiting enzymes of heme degradation and heme synthesis respectively. They may be involved in the mechanism by which the active agent of the invention suppresses the endocrine system.

What is claimed is:

1. A method of limiting the production of estrogenic steroidal hormones in animals in need of such limitation which comprises parenteral administration of from 5 to 50 um/kg b.w. of cobalt protoporphyrin or cobalt mesoporphyrin.

2. A method as in claim 1 wherein cobalt protoporphyrin is administered.

3. A method as in claim 1 wherein cobalt mesoporphyrin is administered.

4. A method as in claim 2 wherein the hormone is an estrogenic steroid.

5. A method as in claim 3 wherein the hormone is an estrogenic steroid.

* * * * *